(12) United States Patent
Fujimoto et al.

(10) Patent No.: US 12,274,415 B2
(45) Date of Patent: Apr. 15, 2025

(54) ENDOSCOPE APPARATUS FOR TRANSMITTING AN ENDOSCOPE IMAGE AS AN OPTICAL SIGNAL

(71) Applicant: OLYMPUS CORPORATION, Tokyo (JP)

(72) Inventors: Takehide Fujimoto, Tokyo (JP); Makoto Tsunakawa, Toda (JP); Keisuke Tsutsui, Kawaguchi (JP); Nanako Ubayama, Tama (JP)

(73) Assignee: OLYMPUS CORPORATION, Tokyo (JP)

( * ) Notice: Subject to any disclaimer, the term of this patent is extended or adjusted under 35 U.S.C. 154(b) by 356 days.

(21) Appl. No.: 17/878,237

(22) Filed: Aug. 1, 2022

(65) Prior Publication Data

US 2022/0386849 A1    Dec. 8, 2022

Related U.S. Application Data

(63) Continuation of application No. PCT/JP2020/004184, filed on Feb. 4, 2020.

(51) Int. Cl.
*A61B 1/00* (2006.01)

(52) U.S. Cl.
CPC ...... *A61B 1/00009* (2013.01); *A61B 1/00013* (2013.01); *A61B 1/00165* (2013.01)

(58) Field of Classification Search
CPC . A61B 1/051; A61B 1/00013; A61B 1/00096; A61B 1/00163; A61B 1/00009;

(Continued)

(56) References Cited

U.S. PATENT DOCUMENTS

| 11,304,599 B2 * | 4/2022 | Komoro | G02B 23/24 |
| 11,317,897 B2 * | 5/2022 | Okada | A61B 8/12 |

(Continued)

FOREIGN PATENT DOCUMENTS

| EP | 3199093 A1 | 8/2017 |
| JP | H0751223 A | 2/1995 |

(Continued)

OTHER PUBLICATIONS

International Search Report dated Apr. 7, 2020 issued in PCT/JP2020/004184.

*Primary Examiner* — John P Leubecker
*Assistant Examiner* — Li-Ting Song
(74) *Attorney, Agent, or Firm* — Scully, Scott, Murphy & Presser, P.C.

(57) ABSTRACT

An endoscope apparatus capable of transmitting an endoscope image as an optical signal includes: an electronic component that includes a reception circuit configured to receive an electric signal outputted from an image pickup device and supply the electric signal to a conversion device; a printed board provided with the electronic component; a shielding member that covers at least the reception circuit; a first path via a ground connection line that is provided for the electronic component, and electrically connects the shielding member to a ground; and a second path via a conductive portion that electrically connects the shielding member to the ground, wherein an impedance of the second path is lower than an impedance of the first path.

3 Claims, 4 Drawing Sheets

(58) Field of Classification Search
CPC ...... A61B 1/00165; G02B 23/24–2469; G01R 31/50–52
See application file for complete search history.

(56) References Cited

U.S. PATENT DOCUMENTS

| | | | | |
|---|---|---|---|---|
| 2011/0103028 | A1* | 5/2011 | Malo | H04M 1/0277 361/753 |
| 2012/0206583 | A1* | 8/2012 | Hoshi | A61B 1/042 348/76 |
| 2016/0211919 | A1 | 7/2016 | Urakawa et al. | |
| 2018/0199802 | A1* | 7/2018 | Hagihara | A61B 1/00018 |
| 2018/0249896 | A1* | 9/2018 | Mikami | A61B 1/044 |

FOREIGN PATENT DOCUMENTS

| | | | |
|---|---|---|---|
| JP | 5851661 | B1 | 2/2016 |
| JP | 2016209542 | A | 12/2016 |
| WO | 2016047172 | A1 | 3/2016 |
| WO | 2019058634 | A1 | 3/2019 |
| WO | WO-2020065757 | A1 * | 4/2020 |
| WO | WO-2024214613 | A1 * | 10/2024 |

* cited by examiner

ENDOSCOPE APPARATUS FOR TRANSMITTING AN ENDOSCOPE IMAGE AS AN OPTICAL SIGNAL

CROSS REFERENCE TO RELATED APPLICATION

This application is a continuation application of PCT/JP2020/004184 filed on Feb. 4, 2020, the entire contents of which are incorporated herein by this reference.

BACKGROUND OF THE INVENTION

1. Field of the Invention

The present invention relates to an endoscope apparatus and, in particular, to an endoscope apparatus capable of transmitting an endoscope image as an optical signal.

2. Description of the Related Art

An endoscope that picks up an image of an object in a subject, and an endoscope apparatus that includes a video processor or the like that applies predetermined image processing to an observed image of the object picked up through the endoscope and outputs the processed image, have been widely used in a medical field, an industrial field and the like.

As for such an endoscope apparatus, conventionally, a technique that adopts a pulse transformer component or the like conforming to the ISO (International Organization for Standardization) standards in order to conform to the IEC (International Electrotechnical Commission) standards, and transmits a video signal has been known.

On the other hand, in recent years, in the field of endoscope apparatuses, with increase in the number of pixels of an image pickup device, a large amount of video signals has been required to be transmitted at high speed. However, conventional transmission paths using metal wires have a problem in that transmission at a high rate (e.g., several gigahertz) is difficult, and additionally measures against emission of electromagnetic waves are complicated (high cost, and high difficulty). In such situations, in recent years, an apparatus that adopts a module of an optical transmission scheme called active optical cables (AOC), as transmission means of video signals, has been proposed accordingly.

The active optical cable (AOC) described above is configured by, for example, integrally providing connecters that internally include optical transceivers (electro-optic conversion devices) at the respective ends of an optical cable configured of an optical fiber. The connectors provided at both the ends of the optical cable each include: a receptacle for connection to a predetermined printed board or the like; and a plug including an electro-optic conversion device that converts, into an optical signal, an electric signal received by a reception circuit included in the receptacle. As described above, the active optical cable (AOC) transmits the optical signal converted by the electro-optic conversion device, to a transmission destination via the optical fiber. Accordingly, the AOC can transmit a large amount of data at high speed.

The active optical cable (AOC) also has an advantage capable of patient insulation to conform to medical instrument regulations.

The active optical cable (AOC), with which the plugs are formed to have a conductive case shape, has a role of an electromagnetic shield that protects circuits (transceiver circuits etc.) and the electro-optic conversion devices in the cases, from electromagnetic waves that are applied from the outside and generate noise.

Here, noise that the exterior (electromagnetic shield) of each plug receives is allowed to flow to a ground pattern or a ground layer of the printed board mounted with the receptacle via an electric terminal of the receptacle.

SUMMARY OF THE INVENTION

An endoscope apparatus of one aspect of the present invention is an endoscope apparatus capable of transmitting an endoscope image as an optical signal, the endoscope apparatus including: a conversion device configured to convert, into an optical signal, an electric signal outputted from an image pickup device provided in an endoscope; a reception circuit configured to receive the electric signal, and supply the electric signal to the conversion device; an electronic component that includes the reception circuit; a printed board provided with the electronic component; a shielding member that covers at least the reception circuit; a ground connection line that is provided for the electronic component, and electrically connects the shielding member to a ground; and a conductive portion that electrically connects the shielding member to the ground, wherein an impedance of a second path that transmits electromagnetic waves received by the shielding member to the ground through the conductive portion is lower than an impedance of a first path that transmits the electromagnetic waves received by the shielding member to the ground through the ground connection line.

DETAILED DESCRIPTION OF THE PREFERRED EMBODIMENT

Hereinafter, an embodiment of the present invention is described with reference to the drawings.

Figure 1:
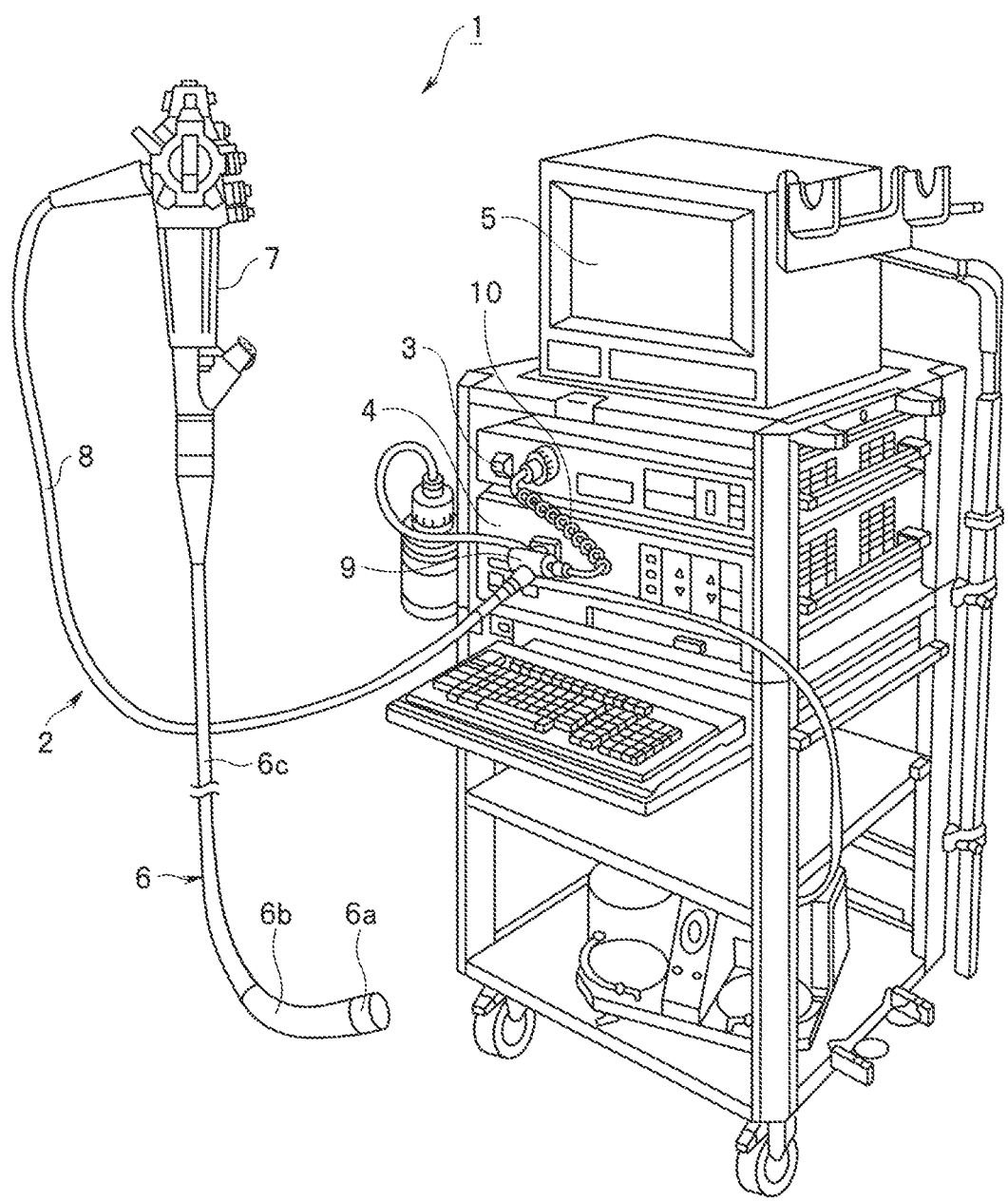
FIG. 1 is an external view showing a configuration of an endoscope system according to one embodiment of the present invention.
Figure 2:
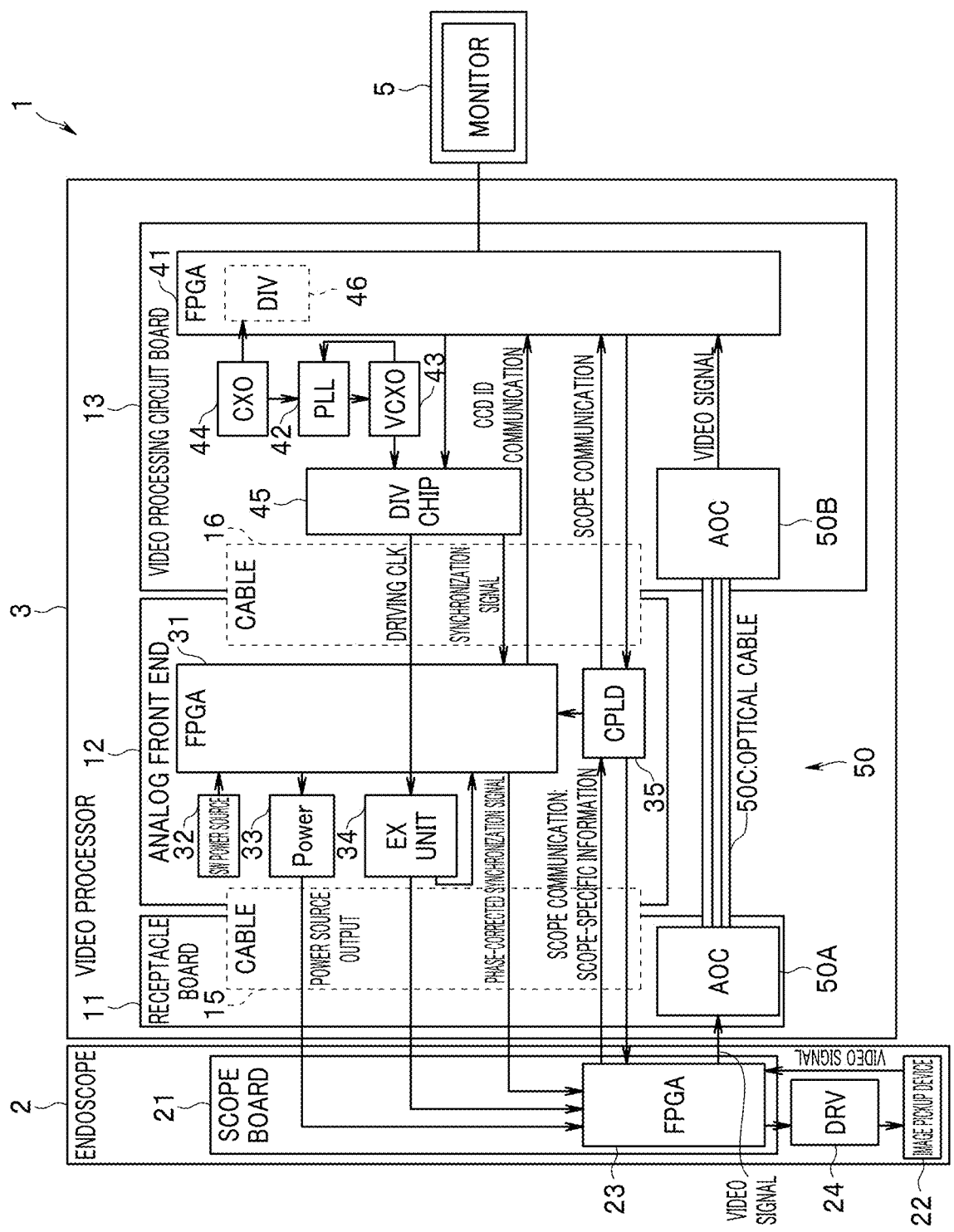
FIG. 2 is a block diagram showing an electric configuration of the endoscope system of one embodiment.

FIG. 1 is an external view showing a configuration of an endoscope system according to one embodiment of the present invention. FIG. 2 is a block diagram showing an electric configuration of the endoscope system of the embodiment.

As shown in FIGS. 1 and 2, an endoscope system 1 of the present embodiment includes: an endoscope 2 that observes a subject and picks up an image; a video processor 3 that is connected to the endoscope 2, receives a picked-up image signal from the endoscope 2, and applies predetermined image processing, a light source apparatus 4 that supplies illumination light for illuminating the subject; and a monitor apparatus 5 that displays an observed image according to the picked-up image signal.

<Configuration of Endoscope 2>

The endoscope 2 is configured by including: an elongated insertion portion 6 to be inserted into a body cavity or the like of a subject; an operation portion 7 that is provided on a proximal end side of the insertion portion 6, is gripped by a surgeon to perform an operation; and a universal cord 8, of which one end portion is provided, so that the cord extends from a side portion of the operation portion 7.

The insertion portion 6 is configured by including: a rigid distal end portion 6a provided on a distal end side; a bending portion 6b that is provided at a rear end of the distal end portion 6a and is freely bendable; and a flexible tube portion 6c that is provided at a rear end of the bending portion 6b, is elongated and has flexibility.

On the proximal end side of the universal cord 8, a connector 9 is provided. The connector 9 is configured to be detachably connected to a light source apparatus 4. Furthermore, one end of a connection cable 10 is connected to an electric contact portion provided on a side surface of the connector 9. The connection cable 10 internally includes, for example, a signal line that transmits a picked-up image signal from an image pickup device (CMOS image sensor) 22 (see FIG. 2) of the endoscope 2, and a connector portion at the other end is allowed to be connected to the video processor 3.

Note that the connector 9 is provided with an AFE (not shown), an FPGA (S-FPGA) 23 for a scope, and a scope board 21 mounted with a memory unit (not shown) that stores predetermined ID information unique to the endoscope 2.

As shown in FIG. 2, the endoscope 2 includes: a non-illustrated objective optical system that is provided at the distal end portion 6a of the insertion portion 6 and includes a lens on which an object image is incident; the image pickup device (CMOS image sensor) 22 provided on an image-forming plane of the objective optical system; and a driver (DRV) 24 that drives the image pickup device 22.

The image pickup device 22 is a solid-state image pickup device configured of a CMOS image sensor in the present embodiment as described above, and is configured to photoelectrically convert the object image, and output a predetermined picked-up image signal to a subsequent stage.

The image pickup device 22 in the present embodiment is configured to be supplied with a plurality of power source voltages (e.g., a digital power source voltage, an interface power source voltage, and an analog power source voltage) generated by the video processor 3, and be driven by a predetermined drive clock pulse signal transmitted also from the video processor 3.

As described above, the endoscope 2 includes the scope FPGA (S-FPGA) 23 on the scope board 21 provided in the connector 9. The S-FPGA 23 is configured of a so-called FPGA (field programmable gate array), and forms a timing adjustment unit that is subjected to an operation control from the video processor 3, and performs various types of timing adjustment.

The timing pulse adjustment unit in the S-FPGA 23 receives drive clock pulses generated by a clock generation unit in the video processor 3, generates various timing pulse signals pertaining to driving of the image pickup device 22, and transmits the signals to the driver 24. The driver 24 is configured to drive the image pickup device 22 according to the timing pulse signals.

The S-FPGA 23 receives a video signal from the image pickup device 22, and transmits the signal to the video processor 3. In the present embodiment, the video signal is transmitted to a reception circuit 51A (see FIG. 3) in an AOC connector 50A of the active optical cable (AOC) provided for the video processor 3.

<Configuration of Video Processor 3>

Returning to FIG. 2, the endoscope system 1 of the present embodiment includes the video processor 3 that is connected to the endoscope 2, receives the picked-up image signal, and applies predetermined image processing.

The video processor 3 in the present embodiment is a control apparatus connected to the endoscope, and includes a receptacle board 11, an analog front end board 12, and a video processing circuit board 13.

The receptacle board 11 includes each terminal group to which the connection cable 10 extending from a side surface of the connector 9 of the endoscope 2, and is connected to the analog front end board 12 by a cable 15.

The receptacle board 11 is provided with the aforementioned AOC connector 50A constituting the active optical cable (AOC) 50, and is configured to receive a video signal from the endoscope 2. Note that the AOC connector 50A is described later in detail.

The analog front end board 12 is a circuit that adjusts publicly known analog signals, and in the present embodiment, for example, includes a function of applying predetermined phase correction and the like to a synchronization signal and a driving clock (CLK) generated in a subsequent-stage circuit, and of outputting the phase-corrected synchronization signal and driving CLK to the endoscope 2. Note that the analog front end board 12 is connected to the receptacle board 11 by the cable 15, and is connected to the video processing circuit board 13 by a cable 16.

In the present embodiment, the analog front end board 12 includes an AFE FPGA (AFE-FPGA) 31 configured of an FPGA (field programmable gate array), a switching power source (SW power source) 32, a various-type power source unit (power) 33, a various-type processing signal output unit (Ex unit) 34, a CPLD 35, and the like.

The AFE-FPGA 31 is supplied with power from the SW power source 32, controls the power 33, i.e., the power source unit, and generates and outputs various power sources for driving the endoscope 2. The AFE-FPGA 31 receives the driving CLK generated by the video processing circuit board 13 on the subsequent stage, and transmits the driving CLK to the S-FPGA 23 of the endoscope 2 via the Ex unit 34. Furthermore, the AFE-FPGA 31 receives the synchronization signal from the video processing circuit board 13, and transmits the appropriately phase-corrected synchronization signal to the S-FPGA 23 of the endoscope 2.

The CPLD 35 is configured of a complex-programmable logic device (CPLD), and is responsible for communication of scope-specific information and predetermined picked-up image information between the video processing circuit board 13 (M-FPGA 41) and the endoscope 2 (S-FPGA 23), etc., in the present embodiment.

The video processing circuit board 13 includes a function of applying predetermined video processing to a video signal from the endoscope 2, and outputting the signal to the monitor apparatus 5 in the subsequent stage. Note that the video processing circuit board 13 is connected to the analog front end board 12 by the cable 16.

The video processing circuit board 13 includes the main FPGA (M-FPGA) 41 configured of an FPGA (field programmable gate array), a crystal oscillator (CXO) 44, a PLL circuit 42, a voltage-controlled crystal oscillator (VCXO) 43, a divider circuit (DIVCHIP) 45, and the like.

The M-FPGA 41 includes a function of applying predetermined image processing to the video signal transmitted from the endoscope 2 through the active optical cable (AOC) 50, and outputting the signal to the monitor apparatus 5.

The M-FPGA 41 includes a divider circuit (DIV) 46 that receives an oscillation signal from the CXO 44 and divides the signal into a predetermined frequency, and generates various synchronization signals, based on a clock signal divided by the divider circuit 46, and outputs the signals to the divider circuit (DIVCHIP) 45.

The divider circuit (DIVCHIP) 45 generates the driving CLK for driving the image pickup device 22 of the endoscope 2, based on the oscillation signals from the PLL circuit 42 and the voltage-controlled crystal oscillator (VCXO) 43 having received the oscillation signal from the CXO 44, and outputs the driving CLK to the AFE-FPGA 31 on the analog front end board 12. Furthermore, the divider circuit (DIVCHLP) 45 outputs the synchronization signal received from the M-FPGA 41 described above to the AFE-FPGA 31.

On the other hand, the M-FPGA 41 is configured to be capable of detecting an abnormal state of a picked-up type by receiving a detection result (CCDID signal) of the AFE unit from the AFE-FPGA 31, and receiving a scope communication signal (i.e., scope information from the endoscope 2) from the CPLD 35. In a case of the abnormal state, the M-FPGA 41 outputs a drive stop signal to the endoscope 2 via the CPLD 35 and the AFE-FPGA 31.

The video processing circuit board 13 is provided with an AOC connector 50B. The AOC connector 50B is an AOC connector that constitutes the active optical cable (AOC) 50 described above, and is provided on the opposite side of the AOC connector 50A with intervention of an optical cable 50C. Note that the AOC connector 50B is described later in detail.

<Active Optical Cable (AOC) 50>

Next, the configuration of the active optical cable (AOC) 50 adopted in the endoscope system 1 of the present embodiment is described with reference to FIGS. 3 and 4 besides FIG. 2.

As shown in FIG. 2, the video processor 3 in the endoscope system 1 of the present embodiment includes the active optical cable (AOC) 50 that transmits the video signal according to an optical transmission scheme between the receptacle board 11 and the video processing circuit board 13. The active optical cable (AOC) 50 is configured by integrally providing the connectors (the AOC connector 50A and the AOC connector 50B) internally including an electric signal and optical signal conversion device (conversion device 53: see FIG. 3) at both the ends of the optical cable 50C configured of an optical fiber.

The AOC connector 50A is provided on the receptacle board 11, and is configured to receive the video signal (electric signal) from the S-FPGA 23 in the endoscope 2 when the video processor 3 is connected to the endoscope 2, convert the signal into an optical signal, and subsequently output the signal to the optical cable 50C.

The optical cable 50C is made into a cable using a multi-mode optical fiber, and is configured integrally with the AOC connector 50A and the AOC connector 50B provided at both the ends. The video signal converted into the optical signal by the AOC connector 50A is transmitted to the AOC connector 50B.

The AOC connector 50B is provided on the video processing circuit board 13, and is configured to receive the video signal (optical signal) from the endoscope 2 transmitted via the optical cable 50C, convert the video signal into the electric signal and output the electric signal to the M-FPGA 41.

Figure 3:
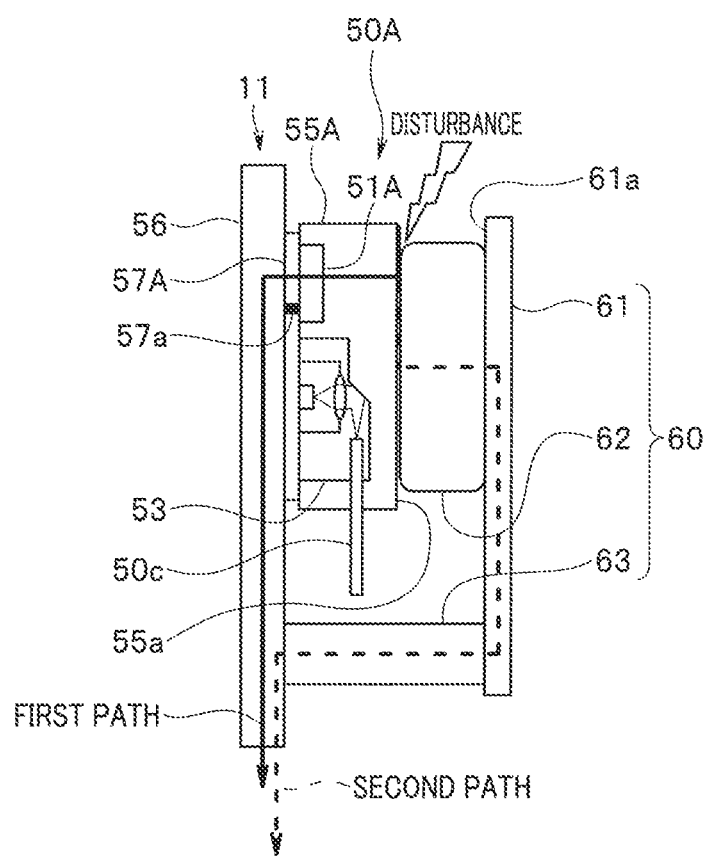
FIG. 3 is a side view showing a configuration of a connector (including a reception circuit) for an active optical cable (AOC) provided in a video processor and a conductive portion in contact with the active optical cable (AOC) in the endoscope system of one embodiment.

FIG. 3 shows the configuration of the AOC connector 50A included in the active optical cable (AOC) 50, and a situation where a conductive portion 60 is in contact with the AOC connector 50A. FIG. 4 shows a situation where the conductive portion 60 is in contact with the AOC connector 50B included in the active optical cable (AOC) 50.

As shown in FIG. 3, the AOC connector 50A includes: a conversion device 53 that converts the electric signal output from the image pickup device 22 provided in the endoscope 2 into an optical signal, and transmits the signal to the optical cable 50C; a reception circuit 51A that receives the electric signal from the endoscope 2, and supplies the electric signal to the conversion device 53; a receptacle 57A that includes the reception circuit 51A; and a shielding member 55A that is a plug covering the reception circuit 51A and the conversion device 53.

On the other hand, as shown in FIG. 3, the AOC connector 50B includes: a conversion device 53 that converts the video signal of the optical signal through the optical cable 50C into an electric signal; a transmission circuit 51B that transmits, to the M-FPGA 41, the video signal converted into the electric signal by the conversion device 53; a receptacle 57B that includes the transmission circuit 51B; and a shielding member 55B that is a plug covering the transmission circuit 51B and the conversion device 53.

The shielding member 55A and the shielding member 55B each have an outer surface 55a that is of the exterior portion and is formed of a conductive layer, and shields the reception circuit 51A or the transmission circuit 51B and the conversion device 53 that are included.

Note that the shielding member 55A and the shielding member 55B are configured so as to cover the reception circuit 51A or the transmission circuit 51B and the conversion device 53 in the present embodiment. However, the members may be at least cover the reception circuit 51A or the transmission circuit 51B.

The receptacle 57A is provided integrally with the reception circuit 51A, and includes a plurality of electric wires that include the ground connection line 57a pertaining to the reception circuit 51A, and the electric wires including the ground connection line 57a are connected to a printed board 56 in the receptacle board 11.

On the other hand, the receptacle 57B is provided integrally with the transmission circuit 51B, and includes a plurality of electric wires that include the ground connection line 57a pertaining to the transmission circuit 51B, and the electric wires including the ground connection line 57a are connected to a printed board 56 in the video processing circuit board 13.

Here, the ground connection line 57a on the receptacle 57A is configured to be electrically connected to the conductive outer surface 55a of the exterior portion in the shielding member 55A described above. Furthermore, the ground connection line 57a on the receptacle 57B is configured to be electrically connected to the conductive outer surface 55a of the shielding member 55B described above, similarly to the above description.

Figure 4:
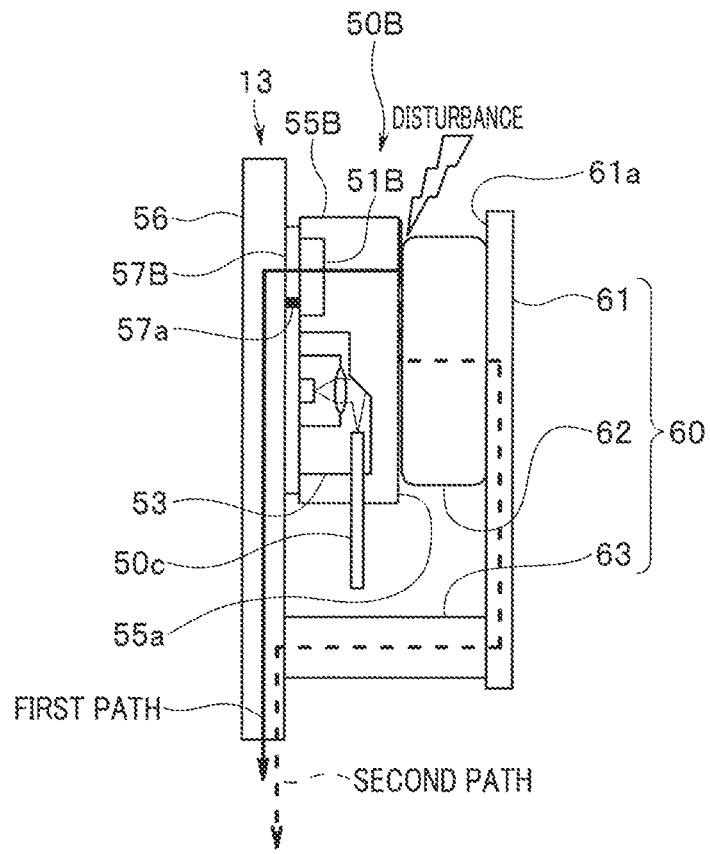
FIG. 4 is a side view showing a configuration of a connector (including a transmission circuit) for an active optical cable (AOC) provided in the video processor and a conductive portion in contact with the active optical cable (AOC) in the endoscope system of one embodiment.

It is assumed that in the AOC connector 50A and the AOC connector 50B having such configurations, for example, as shown in FIG. 3 or 4, noise due to electromagnetic waves is applied to the shielding member 55A or the shielding member 55B from the outside. At this time, for one thing, charges occurring accompanying the noise applied to the shielding member 55A or the shielding member 55B flow to a ground pattern or a ground layer of the printed board 56 through a first path shown in FIG. 3 or FIG. 4.

More specifically, the charges occurring accompanying the noise flow from the shielding member 55A or the shielding member 55B to the ground pattern or the ground layer of the printed board 56 through the ground connection line 57a on the receptacle 57A or the receptacle 57B.

<Conductive Portion 60>

Next, the conductive portions 60 adopted in the AOC connector 50A and the AOC connector 50B in one embodiment of the present invention are described.

As shown in FIGS. 3 and 4, in the present embodiment, the conductive portion 60 includes: a plate-shaped portion 61 formed of a conductive material having a plate-like shape; a gasket 62 in contact with the plate-shaped portion 61; and a screw 63 for causing the plate-shaped portion 61 to engage with the printed board 56.

The plate-shaped portion 61 includes a planar portion 61a that faces the shielding member 55A or the shielding member 55B, and is disposed to be urged by a predetermined pressing force against the shielding member 55A or the shielding member 55B in a state where the gasket 62 intervenes between the planar portion 61a and the conductive layer of the outer surface 55a of the shielding member 55A or the shielding member 55B.

The gasket 62 is made of a conductive material, and is provided between the planar portion 61a of the plate-shaped portion 61 and the opposite surface (outer surface 55a) of the shielding member 55A or the shielding member 55B, as described above.

The screw 63 is formed of a conductive material, and is disposed so that the plate-shaped portion 61 engages with the printed board 56 around a position where the planar portion 61a of the plate-shaped portion 61 is in contact with the gasket 62. By the screw 63, the plate-shaped portion 61 is urged against the shielding member 55A or the shielding member 55B by the predetermined pressing force.

The plate-shaped portion 61 is pressed against the outer surface 55a of the shielding member 55A or the shielding member 55B by the predetermined urging force, which reduces the impedance value with the conductive layer of the shielding member 55A or the shielding member 55B.

It is assumed that in the state where the plate-shaped portion 61, the gasket 62 and the screw 63 are disposed as described above, for example, as shown in FIG. 3 or 4, noise due to electromagnetic waves is applied to the shielding member 55A or the shielding member 55B from the outside. At this time, charges occurring accompanying the noise applied to the shielding member 55A or the shielding member 55B flows to the ground pattern or the ground layer of the printed board 56 from the shielding member 55A or the shielding member 55B through a second path passing through the gasket 62, the plate-shaped portion 61 and the screw 63, besides the first path described above.

Next, the flow of charges when noise due to electromagnetic waves is applied to the shielding member 55A or the shielding member 55B from the outside in the AOC connector 50A and the AOC connector 50B in the present embodiment is described.

Figure 5:
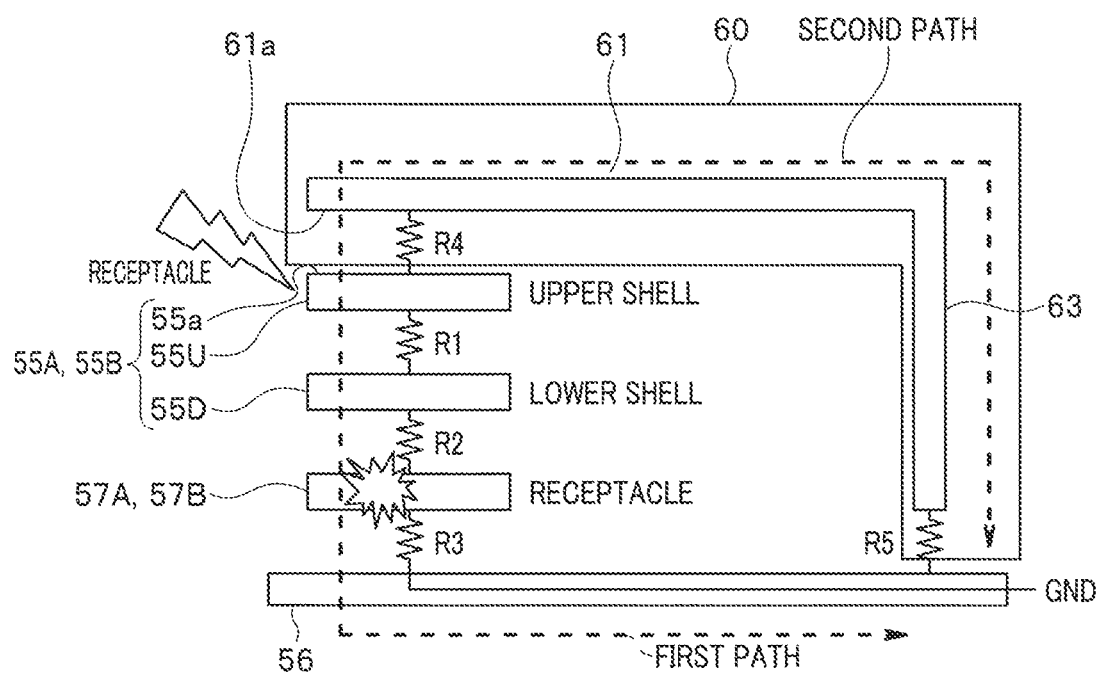
FIG. 5 is a diagram for illustrating the magnitude relationship of impedances according to a first path and a second path in an AOC connector in the endoscope system of one embodiment.

FIG. 5 is a diagram for illustrating the magnitude relationship of the impedances according to the first path and the second path in the AOC connector 50A or the AOC connector 50B in the present embodiment.

Here, to analyze and describe the impedances according to the first path and the second path, as shown in FIG. 5, in the shielding member 55A and the shielding member 55B, a portion including the outer surface 55a in contact with the planar portion 61a of the plate-shaped portion 61 is assumed as an upper shell 55U, and a portion connected to the ground connection line 57a of the receptacle 57A or the receptacle 57B is assumed as a lower shell 55D.

As described above, it is assumed that the external noise is applied around the upper shell 55U of the shielding member 55A or the shielding member 55B. At this time, as shown in FIG. 5, the first path goes through a path along the upper shell 55U, the lower shell 55D, the ground connection line 57a and the ground pattern (or the ground layer) of the printed board 56.

Provided that the impedance of each part of the first path is so that
between the upper shell 55U and the lower shell 55D: R1,
between the lower shell 55D and the ground connection line 57a: R2, and
between the ground connection line 57a and the ground pattern of the printed board 56: R3,
the total impedance of the first path is R1+R2+R3.

On the other hand, the second path goes through the path along the upper shell 55U (outer surface 55a), the gasket 62, the plate-shaped portion 61 (planar portion 61a), the screw 63, and the ground pattern (or the ground layer) of the printed board 56.

The impedances of the gasket 62 and the screw 63 made of conductive materials are substantially zero. Accordingly, provided that the impedance of each part of the second path is so that
between the upper shell 55U (outer surface 55a) and the plate-shaped portion 61 (planar portion 61a): R4, and
between the plate-shaped portion 61 and the ground pattern of the printed board 56: R5, the total impedance of the second path is R4+R5.

Here, in the first path,
between the lower shell 55D and the ground connection line 57a: R2, and
between the ground connection line 57a and the ground pattern of the printed board 56: R3
are each substantially close to a point contact. Accordingly, it is believed that the total impedance of the first path has a relatively large value.

On the other hand, in the second path,
between the upper shell 55U (outer surface 55a) and the plate-shaped portion 61 (planar portion 61a): R4
since surface contact between surfaces with a relatively large area is achieved, the resistance value tends to decrease. Furthermore, as described above, by the urging force due to engagement by the screw 63, the planar portion 61a of the plate-shaped portion 61 and the outer surface 55a of the shielding member 55A or the shielding member 55B (i.e., the upper shell 55U) are in contact with each other with a strong force (even though via the gasket 62). Also in this point, an advantageous effect of reducing the impedance is exerted.

As described above, in the AOC connector 50A and the AOC connector 50B in the present embodiment, the impedance of the second path that transmits electromagnetic waves received by the shielding member 55A or the shielding member 55B to the ground via the conductive portion 60 can be configured lower than the impedance of the first path that transmits electromagnetic waves received by the shielding member 55A or the shielding member 55B to the ground via the ground connection line 57a.

Accordingly, even when strong noise is applied to the shielding member 55A or the shielding member 55B from the outside, charges caused by application of the noise flows to the ground through the second path more preferentially than through the first path. Accordingly, the adverse effect of the noise against the reception circuit 51A or the transmission circuit 51B residing in the first path can be reduced to the minimum.

Consequently, according to the configuration of the present embodiment, advantageous effects are exerted where the adverse effects to the reception circuit 51A or the transmission circuit 51B can be significantly reduced for not only containment of noise based on strong energy, such as of an electric scalpel, but also for containment of noise at a minute level, of which effect more concern has been paid to in recent years, and contribution to improvement in SN ratio of an endoscope image is made.

The present invention is not limited to the embodiment described above, and can be subjected to various changes, modifications and the like in a range without changing the gist of the present invention.

What is claimed is:

1. An endoscope apparatus capable of transmitting an endoscope image as an optical signal, the endoscope apparatus comprising:
    a conversion device configured to convert, into an optical signal, an electric signal outputted from an image pickup device provided in an endoscope;
    a reception circuit configured to receive the electric signal, and supply the electric signal to the conversion device;
    an electronic component that includes the reception circuit;
    a printed board provided with the electronic component;
    a shielding member that covers at least the reception circuit;
    a ground connection line that is provided for the electronic component, and electrically connects the shielding member to a ground; and
    a conductive portion that electrically connects the shielding member to the ground,
    wherein an impedance of a second path that transmits electromagnetic waves received by the shielding member to the ground through the conductive portion is lower than an impedance of a first path that transmits the electromagnetic waves received by the shielding member to the ground through the ground connection line.

2. The endoscope apparatus according to claim 1, further comprising
    an exterior portion that internally includes the electronic component, and the conversion device,
    wherein the shielding member is formed of a conductive layer provided on an outer surface of the exterior portion.

3. The endoscope apparatus according to claim 2,
    wherein the conductive portion includes a plate-shaped portion that includes a planar portion facing the shielding member, and a gasket in contact with the planar portion, and
    the plate-shaped portion is disposed to be urged to the shielding member by a predetermined pressing force in a state where the gasket intervenes between the planar portion and the conductive layer of the shielding member.

* * * * *